United States Patent
van Dongen et al.

(10) Patent No.: US 7,413,862 B2
(45) Date of Patent: Aug. 19, 2008

(54) FRET PROBES AND METHODS FOR DETECTING INTERACTING MOLECULES

(75) Inventors: Jacobus Johannes Maria van Dongen, Nieuwerkerk aan den IJssel (NL); Frank Jakob Theodor Staal, Delft (NL)

(73) Assignee: Erasmus Universteit Rotterdam, Rotterdam (NL)

( * ) Notice: Subject to any disclaimer, the term of this patent is extended or adjusted under 35 U.S.C. 154(b) by 234 days.

(21) Appl. No.: 11/122,776

(22) Filed: May 5, 2005

(65) Prior Publication Data

US 2005/0260660 A1  Nov. 24, 2005

Related U.S. Application Data

(63) Continuation of application No. PCT/NL2003/000777, filed on Nov. 6, 2003.

(30) Foreign Application Priority Data

Nov. 7, 2002 (EP) .................................. 02079667

(51) Int. Cl.
  *C12Q 1/68* (2006.01)
  *C07H 21/02* (2006.01)
  *C07H 21/04* (2006.01)
(52) U.S. Cl. .................... 435/6; 536/23.1; 536/24.3
(58) Field of Classification Search ............ 435/6, 435/7.1; 536/23.1, 24.3
  See application file for complete search history.

(56) References Cited

U.S. PATENT DOCUMENTS

| | | | |
|---|---|---|---|
| 6,235,535 | B1 | 5/2001 | Keinanen et al. |
| 7,081,336 | B2 * | 7/2006 | Bao et al. .................... 435/6 |
| 2002/0081617 | A1 | 6/2002 | Burnanda et al. |
| 2003/0059811 | A1 * | 3/2003 | Djaballah et al. ............ 435/6 |
| 2003/0228603 | A1 * | 12/2003 | Cload et al. .................. 435/6 |
| 2004/0110245 | A1 | 6/2004 | Nagamune et al. |

FOREIGN PATENT DOCUMENTS

| | | |
|---|---|---|
| EP | 1 382 965 A1 | 1/2004 |
| WO | WO 99/18124 | 4/1999 |
| WO | WO 01/33199 A2 | 5/2001 |
| WO | WO 2004/042404 | 5/2004 |

OTHER PUBLICATIONS

PCT International Search Report, PCT/NL03/00777, dated Mar. 5, 2004.
PCT International Preliminary Examination Report, PCT/NL03/00777, dated Jan. 13, 2005.
Lundin et al., "Development of a Time-Resolved Fluorescence Resonance Energy Transfer Assay (Cell TR-FRET) for Protein Detection on Intact Cells," Analytical Biochemistry, 2001, pp. 92-97, vol. 299.
Bader et al., "A cGMP-Dependent Protein Kinase Assay for High Throughput Screening Based pf Time-Resolved Fluorescence Resonance Energy Transfer," Journal of Biomolecular Screening, 2001, pp. 255-263, vol. 6, No. 4.
Szollosi et al., "Application of Fluorescence Resonance Energy Transfer in the Clinical Laboratory: Routine and Research," Cytometry (Communications in Clinical Cytometry), 1998, pp. 159-179, vol. 34.
Kane et al., Development of a Binding Assay for p53/HDM2 by Using Homogenous Time-Resolved Fluorescence, Analytical Biochemistry, 2000, pp. 29-38, vol. 278.

* cited by examiner

*Primary Examiner*—Ethan Whisenant
(74) *Attorney, Agent, or Firm*—TraskBritt

(57) ABSTRACT

This invention relates to the field of detecting interacting molecules. The invention provides a set of a first and a second probe, each such probe provided with a dye allowing energy transfer; at least one probe provided with a reactive group allowing juxtaposing the first and second probe. A method is provided for detecting at least two interacting molecules at the single cell level using of a set of probes according to the invention.

23 Claims, 2 Drawing Sheets

FRET PROBES AND METHODS FOR DETECTING INTERACTING MOLECULES

CROSS-REFERENCE TO RELATED APPLICATION

This application is a continuation of PCT International Patent Application No. PCT/NL2003/000777, filed on Nov. 6, 2003, designating the United States of America, and published, in English, as PCT International Publication No. WO 2004/042404 A1 on May 21, 2004, which itself claims priority to European Patent Application 02079667.8, filed on Nov. 7, 2002, the contents of the entirety of both which are incorporated by this reference.

TECHNICAL FIELD

This invention relates generally to biotechnology, and more particularly to the field of detecting interacting proteins and other closely associated molecules. More specifically, the invention relates to assessing close interactions between macromolecules at the single cell level.

BACKGROUND

The recent abundance of genome sequence data has necessitated systematic proteomics to decipher the encoded protein networks that dictate cellular function. These include cell-cell interaction, cell activation, cell cycle, signaling pathways, cell proliferation, differentiation, apoptosis, development and many other cellular functions. Initial steps in elucidating the function of an uncharacterized gene product, i.e. a novel protein, often involve studying its interaction with other proteins. Whereas the elucidation of a protein network provides a wealth of information regarding the players, insight into interactions between individual molecules is essential for understanding the contribution of each molecule to a molecular network.

Co-localization studies are often employed to monitor the proximity of one protein of interest to another protein of interest. Co-localization data are also useful as a means of evaluating protein information inferred from genetic data, for instance, supporting or refuting putative protein interactions suggested from for example a yeast two-hybrid analysis. Co-localization of intracellular proteins can be assessed by use of differentially labeled antibodies specifically reactive with endogenous proteins of interest which can be visually detected by fluorescence microscopy via immunofluorescence. Hereto, fixed cells are treated first with a set primary antibodies specific to proteins of interest, and then with a set of secondary antibodies conjugated with fluorescent dye. Antibodies directly conjugated with a fluorescent dye may also be used. Those dyes should differ in excitation and emission wavelength, so that they can be excited independently and observed in separate fluorescent channels. Alternatively, genes encoding the proteins of interest may be fused to a reporter gene encoding a reported protein, like green fluorescent protein (GFP), or tagged with an epitope, such as Myc or HA. Reporters and epitope tags are fused routinely to either the N or C termini of target genes. Dyes specific to membranes or nucleic acids may additionally be used to reveal the cell organelles, for instance, the nucleus can be visualized by DNA staining with DAPI. Images are generally collected on a confocal microscope which ensures that observed proteins are in the same focal plane, and therefore co-localization, if any, is real. Co-localization is revealed by overlap in colors.

However, it should be emphasized that the resolution of confocal microscopy only allows one to detect a global co-localization of proteins and does not necessarily prove close interaction. Overlapping colors do not necessarily imply interacting proteins, i.e. positioning of the proteins within a very short distance, for instance in the range of 3 to 100 Ångstrom. Therefore, co-localization studies routinely require supplementary analysis to investigate whether co-localized molecules represent truly interacting partners. Typical standard biochemical techniques to evaluate putative interacting molecules include co-immunoprecipitation experiments, affinity pull down assays and affinity chromatography.

Co-localization of cell surface molecules, for example, proteins A and B, can also be determined via so-called "patching/capping" experiments. Briefly, upon addition of a multivalent ligand for protein A to viable cells, a clump or patch of protein A molecules assembles in the membrane. If the cell is alive and metabolizing actively, patches are formed which can further assemble into a cap in a process called "capping", preferably occurring at 37 degrees Celsius. The patches/cap can be stained by indirect fluorescence staining procedures. Subsequently, cells may be counterstained at 4 degrees Celsius (to retain the patches/cap) with a dye-conjugated antibody against protein B to evaluate whether protein B has moved together i.e. is co-localized with the "patched/capped" protein A or whether protein B is still diffusely distributed on the cell surface.[1] Although this method works in practice for assessing co-localization of surface membrane proteins, it is time consuming, needs experience and can only be evaluated by dye microscopy, not by flow cytometry. Furthermore, microscopic procedures are not suitable as a high throughput method for the evaluation of interacting molecules.

A particularly elegant method to detect closely interacting molecules involves fluorescence resonance energy transfer (FRET). In FRET, a dye (called a "donor") transfers, after excitation by a light source, its energy to another dye (called "acceptor"). The energy transfer occurs when the emission spectrum of the donor dye overlaps significantly with the excitation spectrum of the acceptor. Sufficiently close juxtaposition of the two dyes, generally closer than 100 Ångstrom, but preferably closer than 50 Ångstrom, is essential for energy transfer between the donor/acceptor pair. One Ångstrom, a metric unit of length, is equal to 0.1 nanometer or $10^{-10}$ meter. FRET is usually based on the interaction between donor and acceptor dyes that are both fluorescent. However, FRET can also be detected by the quenching of donor fluorescence using a nonfluorescent acceptor dye. Nonfluorescent acceptor dyes are in general advantageous because they eliminate the background fluorescence that results from direct acceptor excitation. In the present invention, it is possible to monitor juxtaposed probes on interacting molecules using a fluorescent donor dye and a nonfluorescent acceptor dye. Specific binding of a set of probes to non-interacting molecules will give a basal fluorescence signal. Upon close interaction of the molecules, FRET between the probes will quench the donor fluorescence. Rather than measuring an increase in acceptor fluorescence, use of a nonfluorescent acceptor involves measuring a decrease in donor fluorescence. Generally, detection of a decreased signal is less sensitive compared to detection of an increased signal. Therefore, a method according to the invention is preferably practiced using a fluorescent donor and a fluorescent acceptor dye.

FRET energy transfer efficiency is inversely proportional to the sixth power of the distance between the donor and the acceptor. FRET, first described by Förster, has become extremely important for modern cell biology because FRET allows to measure distances between molecules on a scale of a few nanometers. This is far below the resolution limit of modern optical far field microscopy, which currently is at approximately 100 nm. FRET technology has been used for detection of various individual (bio)molecules. For example, U.S. Pat. No. 6,235,535 discloses a fluorescence-based immunoassay method for the detection of an analyte in a biological sample. The method is based on the ability of a multivalent analyte (antigen) to induce aggregation of identical receptor molecules (antibodies) labeled with a fluorophore, which molecules are immobilized onto yet freely mobile on a lipid membrane. Antigen-induced aggregation of the receptors causes FRET to take place. Also in U.S. patent Publication 2002/0081617, antibodies directed to the same epitope but labeled with either a donor of acceptor dye are immobilized, in this case onto beads. Upon addition of an analyte (antigen) of interest, the analyte functions as a bridge and brings a pair of antibodies into close proximity of each other which leads to FRET. Thus, U.S. Pat. No. 6,235,535 and U.S. patent Publication 2002/0081617 both relate to the detection or measurement of an analyte using immobilized, dye-conjugated probes and FRET-based detection methods. Since the probe sets of U.S. Pat. No. 6,235,535 and U.S. patent Publication 2002/0081617 are directed to a single molecule or molecular epitope, they are essentially not suitable for detecting distinct interacting molecules.

The extreme sensitivity of the FRET process on the distance between molecules renders it a very useful tool for the resolution of intracellular protein arrangements and protein dynamics. The presence of FRET indicates intermolecular interaction since it is observable only for nanometer-scale fluorophore distance. This implies in particular that simple co-localization of two molecules, e.g. proteins, is not sufficient to yield energy transfer. FRET is a technique that can give clear, unambiguous answers to questions about protein-protein interactions. FRET measurements can be used to determine protein interactions at the cell surface[2]. The "green revolution" initiated by the introduction of the green fluorescent protein (GFP) from *Aequorea victoria* and the later developments of GFP-mutants possessing different spectral properties offered the possibility of simultaneous expression of different proteins, artificially tagged with fluorescent donor and acceptor domains in the same cell.[3,4] This allowed measurement of their interactions by FRET. The combination of Cyano Fluorescent Protein (CFP) (donor) and Yellow Fluorescent Protein (YFP) (acceptor)—tagged proteins is often used. This FRET pair can be used to monitor the proximity of the two attached fluorescent tags in 3-6 nm. Co-expression of CFP- and YFP-tagged proteins has been successfully used to analyze short time changes in protein-protein interactions, e.g. oligomerization, co-localization, complex formation, activation of kinases and mapping of enzyme activities in living cells. FRET technology was also used in a highly specific fluorescence lifetime imaging microscopy (FLIM) method for monitoring epidermal growth factor receptor (EGFR) phosphorylation in cells. EGFR phosphorylation was monitored using a GFP-tagged EGFR and Cy3-conjugated anti-phosphotyrosine antibodies.[5]

Although fluorescently tagged proteins have proven to be very useful, they do have limitations, such as their significant size (>200 amino acids). Also, the overall folding and tertiary structure of a tagged protein may be different from that of the native, non-tagged protein. This may result in different, erroneous interactions with other molecules. Drawing conclusions with respect to the addressed protein-protein interactions on the basis of FRET data between pairs of tagged proteins, as well as performing comparisons with normal cellular functions in living cells, is justified only if the recombinant, tagged proteins behave similar to the corresponding endogenous wild-type proteins. For instance, the expressed fluorescently-tagged protein should reveal the same intracellular distribution as the wild-type protein; the expression of the tagged protein per se should not induce or inhibit cellular functions and the tagged protein expressed in the cell should not create significant background FRET-signal, for example, due to overexpression, pH shift etc. Another major drawback of the use of recombinant, tagged proteins lies in the fact that it requires transfection or co-transfection of a chimeric construct or constructs of interest into a cell and selection of a cell showing adequate expression of a construct to yield a functional protein. Such a system does not allow detection of an endogenous protein and can therefore not be used to evaluate endogenous interacting molecules. One report describes the use of FRET technology to monitor ligand-induced dimerization of an endogenous cell surface receptor by means of a receptor-specific antibody that was directly conjugated to either the donor dye FITC or the acceptor dye Cy3.[6] The ability of a ligand to induce receptor dimerization was assessed by flow cytometric analysis of FRET between FITC and Cy3. A pair of antibody conjugates was used to study cell surface proteins on human lymphocytes: the CD8alpha chain detected by pairs of antibodies against different epitopes; the very late antigen 4 (VLA4), a heterodimeric alpha$_4$beta$_1$ integrin, was detected via FRET between antibody conjugate pairs specific for either integrin beta$_1$ (CD29) or integrin alpha$_4$ (CD49d); association of T-cell receptor (TCR) with a soluble antigen ligand was detected by FRET when anti-TCR antibody and MHC class I/peptide complexes were used. In yet another report, antibody mediated FRET technology was used to measure the interaction of c-kit receptor with its ligand SCF (stem cell factor).[7] Thus far, antibody-mediated FRET technology has not been applied to detect intracellular protein-protein interactions.

FRET technology has also been applied for the detection of a protein-DNA interaction on the basis of a so-called indirect binding principle. For example, it was used to monitor the interaction between the p65 subunit of the transcription factor, NF-kappaB and its DNA binding site. NF-kappaB is of great relevance to the pharmaceutical sector due to its ability to regulate a number of genes involved in various immune and inflammatory responses. As such NF-kappaB has been implicated in several disease states including various viral infections (HIV), arthritis and cancer. An anti-GST antibody labeled with Cy3 (approx. 7-12 dyes per molecule) is allowed to interact with an affinity purified GST fusion protein of p65 and GST (p65GST). A double-stranded DNA (dsDNA) sequence which contains the NF-kappaB binding site was singly labeled with Cy5 at the 5' end of the coding sequence. This was then incubated with a Cy3 labeled antibody and p65GST. The reaction was done either in the presence or absence of unlabeled non-specific or specific competitor dsDNA. In the absence of either competitor, binding by p65-GST resulted in FRET between the Cy3 donor molecules on anti-GST and Cy5 acceptor molecule on dsDNA.

Thus, it would be advantageous to possess a method that allows the detection of interactions between endogenous intracellular proteins and/or other molecules such as nucleic acids, lipids and/or carbohydrate moieties. Particularly challenging is the detection of intermolecular interactions at the single cell level.

DISCLOSURE OF THE INVENTION

The present invention provides the insight that dye-conjugated probes, for instance, antibodies, can be used to detect interacting endogenous molecules when these probes are sufficiently juxtaposed. Provided is a set of at least a first and a second molecular probe, each probe provided, with a dye wherein the dyes together allow energy transfer; at least one probe provided with a reactive group allowing juxtaposing the at least first and second probe wherein the reactive group allows to modulate juxtaposing of the probes such that there is an increased likelihood of energy transfer between them.

According to the invention, a molecular probe is capable of specifically binding to an interacting molecule of interest via its so-called binding domain. Following binding of a at least a first and a second probe to a molecule via the binding domain, a reactive group can be used to modulate juxtapositioning of the probes. A reactive group has no or a minimal tendency to compete with the binding domain for binding to an interacting molecule. Herewith, a set of probes of the invention can be distinguished from known sets of antibody probes which are clustered or juxtaposed by the mere binding to one antigenic molecule or complex. A reactive group preferably remains available for modulating the spatial organization of juxtaposed probes after the probes are bound to interacting molecules.

Further, the invention provides a method for detecting at least two interacting molecules in a cell using a set of at least a first and a second molecular probe, each probe capable of binding to a different molecule, each probe further provided with a dye wherein the dyes together allow energy transfer, at least one probe provided with a reactive group allowing to modulate juxtaposing of the at least first and the second probe such that there is an increased likelihood of energy transfer between the dyes, comprising providing a set of probes, providing a sample comprising a cell, contacting the sample with the probes under conditions that allow juxtaposing of the probes on the interacting molecules, removing any unbound and any non-specifically bound probe and detecting juxtaposition of the probes via FRET to determine the interaction between the molecules.

The method provided is especially suited to assess close interaction between intracellular proteins. However, the method described can also be applied to detect an interaction between other kinds of molecules, like a protein-nucleic acid interaction, provided that a suitable probe is used. A suitable probe is a substance capable of specifically binding to a specific molecule. A specific molecule may be a protein, nucleic acid, lipid, carbohydrate. A nucleic acid may be DNA or RNA. A probe can be a conventional (poly- or monoclonal) or a synthetic antibody or a binding fragment functionally equivalent thereto, such as a Fab', Fab or a single chain Fv fragment. A probe according to the present invention in fact comprises any type of binding molecule capable of specifically binding to or hybridizing with a specific molecule such as a protein, a nucleic acid, a lipid molecule, a carbohydrate moiety or another class of biomolecules.

For example, the invention can be practiced with a nucleic acid probe capable of hybridizing to a specific nucleic acid sequence. Various nucleic acid probes can be used in the invention to identify genetic elements. These include traditional probes such as small strands of deoxyribonucleic acid (DNA) or ribonucleic acid (RNA) as well as a peptide nucleic acid (PNA). PNA is related to, but distinct from, DNA. The chemical structure of PNA differs from DNA in that a peptide-like backbone instead of a phosphate backbone, supports the nucleic acid bases. Nucleic acid probes to be used according to the invention can be selected on the basis of sequence analysis of nucleic acid regions to be investigated. The probes can be synthesized and labeled according to methods known in the art. Successful binding of a probe to a nucleic acid region within a sample identifies the gene segment.

Provided in the invention is a set of at least a first and a second probe each probe provided with a dye allowing energy transfer each probe additionally provided with a reactive group allowing juxtaposing of the first and second probe. In the present context, the term dye refers to a substituent which, in concert with another dye, can be used for energy transfer e.g. FRET analysis. It is preferred that at least one of the dyes is a fluorochrome. To achieve resonance energy transfer, a donor dye molecule must absorb light and transfer it through the resonance of excited electrons to a second dye molecule, the acceptor. For energy transfer to take place, the fluorescence emission wavelength of the donor must be lower than the excitation wavelength of the acceptor; that is, the process must be energetically "downhill". Whereas FRET is usually based on the interaction between donor and acceptor dyes that are both fluorescent, nonfluorescent acceptor dyes may also be used. These can sometimes be advantageous because they eliminate the background fluorescence that results from direct (i.e., nonsensitized) acceptor excitation. Examples of suitable fluorochromes are fluorescein labels, for instance, 5-(and 6)-carboxyfluorescein, 5- or 6-carboxyfluorescein, 6-(fluorescein)-5-(and 6)-carboxamide hexanoic acid and fluorescein isothiocyanate, Alexa Fluor dyes, cyanine dyes such as Cy2, Cy3, Cy5, Cy7, optionally substituted coumarin, R-phycoerythrin, allophycoerythrin, Texas Red and Princeton Red as well as conjugates of R-phycoerythrin and, e.g. Cy5 or Texas Red. See also the website located at probes.com/handbook/tables/1570.html. Other dyes of interest are quantum dot dyes, which come in a nearly unlimited palette of colors.

Examples of suitable dyes are those suitable for analysis by conventional flow cytometry. FRET pairs which can be used for detection by most conventional flow cytometers are discussed in, for example, Szollosi et al.[8] Preferred combinations of fluorochromes for practicing the present invention comprise those dyes used in the classical tandem conjugates, also referred to as duochromes[9].

In a preferred embodiment of the invention, a sample is contacted with two antibodies, one against protein A and the other against protein B to monitor an interaction between protein A and protein B. One antibody is labeled with a FRET donor dye and the other with a FRET acceptor dye. Only when protein A is in close proximity of protein B, e.g. when both are part of a larger protein complex, the two antibodies become sufficiently close together ("juxtaposed") which allows the donor/acceptor pair to induce a detectable FRET fluorescence signal. However, a complete antibody is a large Y-shaped protein molecule, ~150 kDa in size, made up of 2 heavy chains and 2 light chains. Owing to the length of an antibody molecule (300 to 400 Ångstrom) and the flexibility of the hinge region, antibody molecules can bridge a relatively large distance. The flexibility of an antibody may decrease the probability of energy transfer between a pair of dyes that are conjugated to juxtaposed antibody probes. Also, the size of a probe or a dye might interfere with energy transfer via exerting negative steric effects. Furthermore, when preparing a dye conjugate, like a fluorescent probe, it is in general not possible to control the site of conjugation. In case of antibody conjugation, a dye moiety can become attached to different parts of the antibody molecule. Depending on the site of dye-conjugation, the spatial orientation of dyes on probes can be favorable or unfavorable for energy transfer efficiency, i.e., dyes attached to probes need not necessarily be within energy transfer distance of each other. When the PE/APC FRET pair was evaluated for use in antibody-mediated FRET by analysis of interacting cell surface proteins, FRET was detected in all cases albeit that the energy transfer efficiency observed was always less than 10%. Possibly, this was due to steric effects associated with the size and structure of PE and APC. Thus, whereas a close juxtapositioning of FRET probes is a requirement for energy transfer between a donor/acceptor pair, it may not always be sufficient for achieving efficient energy transfer between the dyes attached to the juxtaposed probes, for example, between fluorochrome-conjugated antibodies on interacting molecules or on molecules that are part of a complex.

DETAILED DESCRIPTION OF THE INVENTION

Figure 1:
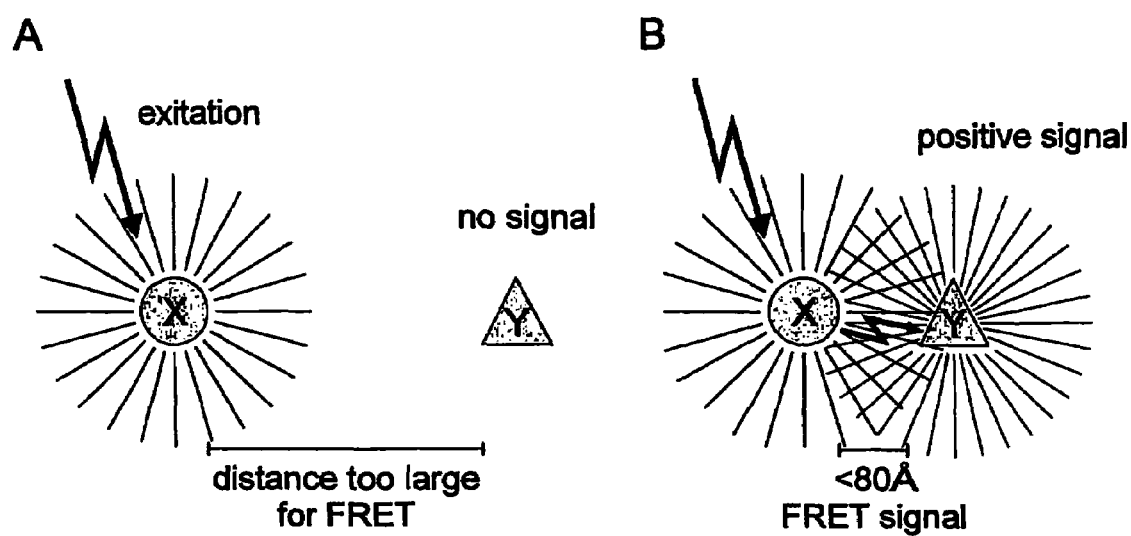
FIG. 1 is a schematic diagram of the principle of fluorescence resonance energy transfer (FRET) with fluorochrome X as donor dye and Y as acceptor dye. The acceptor dye Y will not be excited by the emission light of the donor dye X, if the distance between X and Y is too large. If the distance between the donor and acceptor dye is sufficiently small (<80 Ångstrom but preferably <50 Ångstrom), the emission light of the donor dye X will excite the acceptor dye Y.
Figure 2:
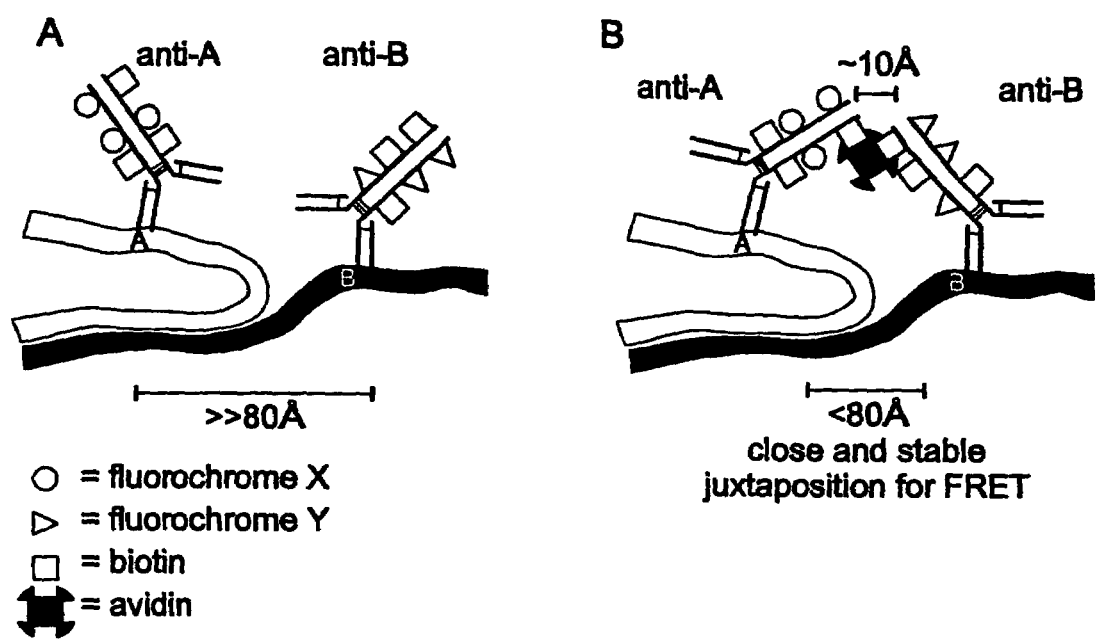
FIG. 2 is a schematic drawing of the closely interacting proteins A and B recognized by an anti-A and an anti-B antibody. Probe A is conjugated with donor dye X and probe B with acceptor dye Y. Furthermore, both probes are conjugated with biotin. After incubation with probes A and B, the probes can be bound together via incubation with avidin, provided that the probes indeed recognize and bind to the closely interacting proteins A and B. This juxtaposition of the two antibody probes (stabilized by the biotin-avidin system) is detectable via the FRET principle (see FIG. 1).

The invention now provides a solution for this problem by providing the insight that juxtaposing of probes can be stabilized and/or enhanced by providing at least one probe with a reactive group. A set of at least a first and a second molecular probe is provided, each probe provided with a dye wherein the dyes together allow energy transfer; at least one probe comprising a reactive group allowing juxtaposing of the at least first and second probe wherein the reactive group allows to modulate juxtaposing the probes such that there is an increased likelihood of energy transfer between them. Use of such a probe set yields an improved sensitivity of detecting juxtaposed probes by measuring energy transfer compared to use of probes without a reactive group. In the present context, the term "reactive group" refers to a moiety which allows modulating the spatial organization of FRET dyes on the probes such that there is an increase in the probability of energy transfer to occur and/or an increase in energy transfer efficiency. The spatial organization refers to both the distance between the dyes as well as to their relative orientation. Modulating the spatial organization includes adjusting and stabilizing the spatial organization of dyes. One of the primary conditions for energy transfer to occur is that donor and acceptor molecules must be in close proximity, typically 2-100 Å. In a preferred embodiment, a reactive group allows bringing the dyes within a distance of 100 Å of each other, more preferably within 50 Å of each other but most preferably within a distance of 20 Å of each other. It is therefore preferred that a reactive group is small, like smaller than 10 kiloDalton (kD), better smaller than 5 kDa, even better smaller than 2 kDa or best smaller than 1 kDa.

A reactive group may be capable of modulating juxtaposed probes (probes bound via their binding domains to interacting molecules) such that there is an increased likelihood of energy transfer between dyes by directly interacting with another probe. For example, a reactive group of a first probe binds to a part of a juxtaposed second probe to form a stable complex between the probes in a spatial orientation that is favorable for FRET to occur. As mentioned above with respect to the site of dye conjugation, it is often not possible to selectively modify a probe with a reactive group at a defined site. The site of modification is mainly determined by the presence and accessibility of a certain residue via which a reactive group is conjugated to a probe, e.g. via primary amines or via thiol groups. Thus, an antibody probe may contain a reactive group at either the constant and/or the variable region of the immunoglobulin. It is conceivable that not every site is equally suitable for interacting with a second probe, for instance, due to steric hindrance. Therefore, it is preferred that a probe is provided with a multiplicity of reactive groups to statistically increase its capacity to interact with another probe.

Provided herein is a method for detecting at least two interacting molecules in a cell using a set of at least a first and a second molecular probe, each probe capable of binding to a different molecule, each probe further provided with a dye wherein the dyes together allow energy transfer, at least one probe provided with a reactive group allowing to modulate juxtaposing the at least first and the second probe such that there is an increased likelihood of energy transfer between the dyes, comprising: providing a set of probes, providing a sample comprising a cell, contacting the sample with the probes under conditions that allow juxtaposing of the probes on the interacting molecules, removing any unbound and any non-specifically bound probe and detecting juxtaposition of the probes via FRET to determine the interaction between the molecules.

In case a first probe can bind directly to at least a second probe, it is preferred to contact the sample with each probe in consecutive steps with extensive intermittent washing procedures to avoid self association between probes. For example, a set of probes A and B are used to detect an interaction between molecule A and B in a sample. Hereto, the sample is contacted with probe A comprising a reactive group to allow recognition of and binding to molecule A. Next, any unbound and any non-specifically bound probe A is removed by repeated washing steps. Subsequently, the sample is contacted with probe B specifically reactive with molecule B under conditions allowing juxtaposing of probe A and B on interacting molecules A and B. Also here, any unbound and any non-specifically bound probe B may be removed by repeated washing steps. A reactive group of probe A may interact with a juxtaposed probe B to modulate the spatial orientation of the dyes present on the probes such that there is an increased likelihood of energy transfer between them. Although this method can be used to detect closely interacting molecules, it shall be clear that such a procedure, involving multiple separate contacting and washing steps, is rather laborious and time-consuming. Moreover, if probes are capable of directly interacting with each other, a significant background signal can be expected because, generally speaking, specific probes bind to their target molecules irrespective of whether these molecules interact. In the example above, a probe A bound to molecule A not interacting with molecule B might still recruit probe B and allow energy transfer between dyes conjugated to probes A and B. Also, if not all unbound probe A is efficiently removed following contacting the sample with probe A, an unwanted interaction between probe A and B can occur upon subsequent contacting the sample with probe B. Both events may result in a detectable energy transfer signal despite the fact that probe B is not juxtaposed to probe A on interacting molecules.

Therefore, in a preferred embodiment of the invention, a reactive group of at least a first probe is not directly or immediately reactive with a second probe in order to avoid self association of the probes. This is also advantageous for an optimal recognition of interacting molecules by the binding domain of each probe and for juxtaposing the probes on the molecules. Moreover, it avoids untimely energy transfer to occur between directly connected or multimerized probes and decreases an aspecific background signal. This is important to ensure that an energy transfer signal truly reflects juxtaposed probes.

The invention provides the insight that a probe comprising a reactive group which does not directly interact with another probe to avoid self association of the probes, is advantageously used in a system comprising a so-called "bridging" substance capable of mediating an interaction between the probes. Such a system allows to modulate juxtaposing the probes such that there is an increased likelihood of energy transfer between the dyes on the probes while minimizing the chance of aspecific and/or untimely interactions between probes. Use of such a set of probes in combination with a bridging substance has several advantages over use of directly interacting probes. First, an improved specificity and reduced background staining can be achieved. After all, for a reactive group to exert its effect via a bridging substance, probes need to be in a close juxtaposition of each other prior to the addition of the substance i.e. resulting from binding of one probe adjacent to another probe on closely interacting molecules. Second, the procedure is faster and easier because no separate contacting steps and washing steps are required for each individual probe. Thus, it permits to contact a sample with a mixture of probes all together in a single action. Likewise, any unbound and any non-specifically bound probes can be removed simultaneously.

A substance may be any kind of compound capable of binding to or modifying a probe, a reactive group and/or a dye to modulate the spatial organization of dyes on juxtaposed probes such that it is favorable for FRET. The substance allows bringing the dyes within a distance of 2 to 100 Ångstrom to each other. The substance is preferably added to a sample following binding of dye-conjugated probes to interacting molecules, in an amount effective to modulate the spatial organization of the dyes on juxtaposed probes. Advantageously, the substance binds to a reactive group with a high specificity and a high affinity. Also, it is preferred that such a substance is relatively small so that the bridging substance only minimally affects the distance between a pair of dyes and the relative orientation of a pair of dyes.

Most preferred, as exemplified herein in the detailed description, is a set of at least a first and a second molecular probe, each probe provided with a dye wherein the dyes together allow energy transfer; each probe provided with a reactive group. A substance is preferably capable of binding, or "bridging", at least two reactive groups. In a preferred embodiment, each probe within a set of probes is provided with the same reactive group. Also, each probe within a set of probes may be provided with a different reactive group but having the same reactivity. This allows the use of one type of bridging substance having at least two identical binding sites for a reactive group.

In one embodiment of the invention, a probe is provided with a multiplicity of reactive groups, like two or three or even up to ten reactive groups, enabling the probe to interact with more than one molecule of bridging substance. Providing a probe with more than one reactive group will theoretically increase the likelihood of an interaction between the probe and a bridging substance. Furthermore, for the ease of practicing the present invention, a suitable reactive group or a derivative thereof is commercially available and can be easily and efficiently attached to a probe.

In accordance with the present invention, a particularly interesting reactive group is biotin, with avidin or streptavidin being a particularly suitable bridging substance. Avidin is an egg-white derived glycoprotein with a molecular weight of about 68000 daltons and a diameter of 8 to 10 Ångstrom. It consists of four identical subunit chains. One avidin or streptavidin molecule can bind four molecules of biotin. Avidin has an extraordinarily high affinity (affinity constant>$10^{15}$ M-1) for biotin. This high affinity assures the user of a rapidly formed and stable complex between avidin and the biotin-labeled probes. The protein streptavidin, produced by the bacterium *Streptomyces avidinii*, has a structure very similar to avidin, and also binds biotin tightly. It often exhibits lower non-specific binding, and thus is frequently used in place of avidin. Once a biotin-avidin complex forms, the bond is essentially irreversible. The biotin-avidin system is widely used and has proven to be very useful in the detection and localization of antigens, glycoconjugates, and nucleic acids by employing biotinylated antibodies, lectins, or nucleic acid probes. As said, a reactive group with such a small size is advantageous for achieving a close distance between a dye pair. Biotin is a vitamin with a molecular weight of only 244 daltons. Furthermore, many biotin molecules can be coupled to a protein, enabling a biotinylated probe to bind more than one molecule of avidin. Avidin, streptavidin and biotin are available from many commercial sources. Various standard procedures for preparing biotin-conjugates are known to those skilled in the art, most of which can be completed within a day. Moreover, commercial biotinylation kits are available which contain all the necessary components for protein biotinylation.

If a set of probes is used wherein each probe is provided with a different reactive group, a suitable substance comprises a molecule capable of binding at least one of each reactive group. Alternatively, such a binding substance comprises a complex of at least two molecules that can be covalently or non-covalently attached to each other, wherein each molecule is capable of binding to a reactive group.

A method according to the invention allows detection of at least two interacting molecules in a cell wherein at least one of the molecules is a proteinaceous substance. In another embodiment, at least one of the molecules is a nucleic acid. In yet another embodiment of the invention, at least one of the molecules is a lipid or a carbohydrate. For example, the invention provides a method to detect the interaction of at least one protein with at least one nucleic acid, such as a DNA-binding protein binding to a specific DNA conformational sequence. The family of DNA-binding molecules includes transcriptional activators or repressor proteins as well as other proteins which bind to double- and/or single-stranded DNA. It also includes specific DNA binding proteins in serum which can be used as markers for malignant diseases. In one embodiment of the invention, a method provided is applied to detect an interaction between a RNA-binding protein and an RNA molecule. RNA-binding proteins are required for translation regulation of gene expression. They are involved in multiple post-translational processes such as the regulation of pre-mRNA splicing, mRNA stability and transport of RNAs between nucleus and cytoplasm. For example, a probe may be used which binds to an RNA-binding protein, like an antibody against a certain splicing factor, in combination with a second probe which recognizes a specific RNA sequence.

A FRET signal is produced only when an interaction takes place between the splicing factor and the RNA. The method provided permits detection of a protein-nucleic acid interaction at the single cell level. To avoid interference with an interaction between molecules of interest, it is preferred that the binding domains of the probes recognize and bind to a region of the molecules of interest that is distinct from the site of interaction between the molecules.

In another embodiment, probes are provided which can detect the interaction between a protein, such as a carbohydrate binding protein (CBP), and a carbohydrate. Protein-carbohydrate interactions are now recognized to be important mediators of cell communication. In the last decade many novel CBPs have been described, and several have been documented to play critical roles in cell trafficking and cell signaling. CBPs recognize carbohydrate ligands on glycoproteins and glycolipids. Included are four large families of CBPs, the siglecs, C-type lectins, galectins and the subset of T cell antigen receptors (TCR) that recognize carbohydrate ligands presented by CD1 and MHC antigen presenting molecules.

In another aspect, the present invention concerns a probe set that can be used for the detection of a protein-lipid interaction, at least one probe being reactive with a protein of interest and at least one probe being reactive with a lipid of interest. The protein may be an enzyme, such as a lipase, a lipid kinase or a lipid phosphatase, interacting with a lipid substrate. The protein probe may comprise an antibody specifically reactive with the protein. A lipid probe according to the invention can be a protein moiety with lipid binding properties. Particularly interesting are those lipid probes which specifically recognize and bind to a lipid molecule which is involved in signal transduction pathways, like phosphoinositide polyphosphates or lipid second messengers diacylglycerol (DAG) or phosphatidic acid (PA). Chimeric green fluorescent protein—pleckstrin homology (PH) domain proteins have been used as a molecular sensor to visualize phosphoinositide polyphosphates (PtdInsP(n)) in living cells. A suitable lipid probe includes a recombinantly produced and purified PH domain. Also included are the DAG-binding domain of protein kinase C (PKC) and the PA—binding region of Raf-1 kinase. A lipid probe comprises an antibody directed against a specific lipid, like a monoclonal antibody specifically reactive with PtdInsP(3).[10] But other lipid probes can be thought of as well.

A set of dye-conjugated probes according to the invention can be used to detect a wide variety of various signal transduction events, either stable or transient, at the single cell level. These include the interaction of a receptor with one or more other molecules, like receptor-ligand interaction, receptor clustering or multimerization, the interaction of a receptor with an intracellular signaling molecule. Other events to be detected using a method provided herein comprise interaction of various signaling molecules with each other, like the docking of a Src-homology 2 (SH2)-containing protein to a specific phosphotyrosine residue in another protein, or the binding of a Src-homology 3 (SH3)-containing protein to proline-rich stretch in another protein. Using specific probes the present method permits to detect interactions between cytoskeletal proteins as well as between nuclear proteins (in the so-called signalosome). Activation of a signal transduction pathway often includes protein phosphorylation by tyrosine kinases and/or serine/threonine kinases. Protein phosphorylations can change enzyme activities and protein conformations. The eventual outcome is an alteration in cellular activity and changes in the program of genes expressed within the responding cells.

In another embodiment, a probe comprises a phosphospecific antibody which specifically recognizes a protein in its phosphorylated state. A phosphorylated residue may be a tyrosine, serine or threonine residue. Phosphospecific antibodies against a wide variety of signaling proteins can be obtained from a number of companies such as Upstate Biotechnology, New England Biolabs, Sigma and many others. For example, a Cy3-labeled phosphotyrosine-specific antibody against the Erb receptor tyrosine kinase can be used to specifically detect the activated form of the receptor. Other examples of suitable probes include a phosphospecific antibody that recognizes only the phosphorylated form of the nuclear transcription factor forkhead in rhabdomyosarcoma (FKHR), protein kinase B (PKB), mitogen-activated protein kinase (MAPK). For several years, analogs of nucleotides that serve as substrates or inhibitors of enzymes, and derivatives that selectively bind to regulatory sites of nucleotide-binding proteins have been used as structural and mechanistic probes for isolated proteins. These type of molecules also represent interesting probes for practicing a method according to the invention.

A method provided herein allows detection of interacting molecules at the single cell level. Single cells can be analyzed using e.g. flow cytometry or fluorescence microscopy. In a preferred embodiment, the detection is performed by flow cytometry. A major advantage of flow cytometry is that it directly gives quantitative data and that it is very rapid (results can be obtained within a few hours). Detecting energy transfer by flow cytometry allows high throughput analysis of interacting molecules. High throughput flow cytometric detection of molecular interactions at the single cell level allows for time course and dose response studies of one or more of the aforementioned interactions, such as signal transduction events, transcription factor interactions. For example, the interaction between the Tcf-1 transcription factor with beta-catenin, or the association of the cytosolic protein tyrosine kinase ZAP-70 with the CD3-zeta chain of the T-cell receptor (TCR), can now be studied at the single cell level using a set of suitable probes according to the invention. In one embodiment, a method provided allows the detection of molecular interaction at the single cell level in permeabilized and/or fixed cells. Furthermore, because the method provided can detect endogenous molecules, it is especially useful to investigate molecular interactions in primary cells. It can for example be used to discriminate between normal and abnormal cells on the basis of one or more of the above-mentioned interactions. Thus, the current invention is preferably practiced with a donor/acceptor pair that is suitable for FRET detection by flow cytometry. A pair commonly used for FRET includes fluorescein isothiocyanate (FITC) and tetramethylrhodamine isothiocyanate (TRITC). However, the sensitivity is poor because of the relatively low molar extinction coefficient and low quantum yield for FITC and TRITC. In addition, laser sources for this pair are usually not found on standard flow cytometers. These problems are not encountered when using the R-phycoerythrin (R-PE)/Allophycocyanin (APC) pair. These dyes are large protein complexes that contain multiple chains and chromophores that are linked covalently. They belong to the group of phycobiliproteins. Phycobiliproteins are produced naturally and are associated with phycobilisomes and are used by different cyanobacteria or algea. The PE/APC pair is very promising because 90% of FRET efficiency may be reached in spite of the sizes of PE and APC. Furthermore, this FRET pair can be detected easily on commercially available flow cytometers such as FACS-Calibur, LSR, and. FAGSVantage equipped with two common lasers (or a diode) in a configuration emitting at 488 and 632 nm.

Detection of energy transfer using flow cytometry or fluorescence activated cell sorting (FACS) offers the possibility to perform rapid, multiparametric analysis of specific individual cells in a heterogeneous population. The detection of multiple fluorescent markers on a cell by flow cytometry provides a powerful tool for single cell analysis and allows subset gating of a target cell population. Selective analysis within a target cell population increases sensitivity of the detection method.

For the detection of molecular interactions in primary cells, it is especially advantageous to use an additional marker to define a target cell population of interest. A number of important biological applications in infectious diseases, minimal residual disease detection and monitoring, and gene therapy typically require the analysis and isolation of rare cells (e.g. hematopoietic stem/progenitor cells) from a large background. A method according to the invention can include intracellular staining or staining of a surface marker to define a target cell population in a mixture of cells comprising staining with a fluorescent marker antibody capable of selectively identifying the cellular marker. The present method flow allows gating of subset of cells that are present in a mixture of cells via immunophenotypic characteristics, i.e. it permits the detection of interacting molecules in a rare population of cells.

In a preferred embodiment, a method is provided to identify and/or isolate rare single cells using multiparameter flow cytometry/cell sorting techniques and to characterize molecular interaction at the single-cell level. A method provided now allows detection of interacting molecules in a mixture of abnormal cells with normal cells to identify and quantitate abnormal cells based on the basis of an aberrant interaction between molecules. Such a method is particularly suited for application to a number of important problems in immune system development, infectious diseases, cancer and gene therapy. Typically, prior to staining a cell sample with a probe set, cell are labeled with at least one relevant dye-conjugated antibody according to standard procedures in order to define a target cell population in a mixture of cells. A mixture of cells comprises living cells. It also comprises permeabilized and/or fixed cells. A method is provided comprising staining a sample for at least one cellular marker to define a target cell population comprising contacting the sample with a compound capable of selectively binding to a cellular marker. In a preferred embodiment, such a compound is directly tagged with a fluorescent dye. A suitable compound comprises a fluorescently labeled antibody or a binding fragment functionally equivalent thereto. Also, a compound capable of selectively binding to a cellular marker can be used which can be detected using a dye-conjugated secondary reagent (e.g. a fluorescently labeled secondary antibody). A cellular marker comprises any kind of intracellular or membrane-bound marker which can be used to distinguish a subpopulation of cells in a mixture of cells. A cellular marker can be a cluster of differentiation (CD) antigen. CD markers are cell surface molecules of among others haemopoietic cells that are distinguishable with monoclonal antibodies. Haemopoietic cells comprise thymocytes, dendritic cells, Langerhans' cells, neutrophils, eosinophils, germinal centre B cells, follicular dendritic cells, plasma cells and bone-marrow cells. For example, suitable cellular markers comprise CD1, CD3, CD4, CD8, CD10, CD19, CD20, CD33, CD34 and CD117. Monoclonal antibodies directed against a large number of human CD markers can be obtained from various suppliers, such as BD Biosciences or Ancell Immunology Research Products, Bayport, USA. Often, antibodies are available that are directly conjugated with a fluorochrome of choice, for example, CD10-PE or CD19-FITC, which is obviously the preferred choice to practice a method according to the invention.

The choice of dye should preferably but not exclusively aim at the usage of two or three dyes for immunophenotyping in addition to the FRET dyes for detection of close interaction of at least two molecules. For example, a FRET probe set according to the invention can be combined with one or more dyes to mediate leukocyte subset gating via immunophenotypic characteristics, for example, CD10, CD19 and CD20 to accurately define subsets of precursor-B-cells in bone marrow, or CD1, CD4 and CD8 to define subsets of thymocytes, or CD34 and/or CD117 to identify stem/precursor cell populations.

In one embodiment, the invention provides a method for detecting at least two interacting intracellular molecules using of a set of probes according to the invention, each probe being reactive with a different molecule comprising providing a sample comprising a cell, whereby the sample will be subject to fixation and permeabilization, contacting the preparation with a set of probes each probe capable of binding to a specific molecule under conditions that allow juxtaposing of the probes on the molecules, removing any unbound and any non-specifically bound probe and. detecting juxtaposition of the probes via FRET. The sample is preferably treated so as to obtain a preservation of the morphology of the material and permeabilization in order to ensure sufficient accessibility of a molecule of interest to a probe. The type of treatment will depend on several factors, for instance on the fixative used, the extent of fixation and the type and properties of the molecules of interest. Fixation may be carried out with a fixative such as formaldehyde. In a preferred embodiment, the method is practiced to detect intracellular molecules that are positioned within a very short distance of each other, for example within 100 Ångstrom, preferably within 50 Ångstrom, more preferably within 20 Ångstrom.

A method is provided wherein a sample comprises a primary cell that is obtained from a biological sample. A biological sample can be a body fluid sample including blood, bone marrow, urine, cerebrospinal fluid (CSF), saliva. It may also be a tissue sample or a tissue homogenate. A sample comprises a cultured cell which may be a cultured primary cell, for example a cultured dermal fibroblast obtained from a skin biopsy. Furthermore, a sample may comprise a cultured cell from an established laboratory cell line, like a HeLa, COS, MCF-7 or a Jurkat cell line, which can be obtained from a number of sources such as the American Type Culture Collection (ATCC; see www.atcc.org for an online catalog).

The invention provides a method to prepare a probe set, comprising contacting each probe with a suitable dye or a derivative thereof to form a conjugate between the probe and the dye and purifying the conjugate from excess dye further comprising contacting at least one probe with a suitable reactive group or a derivative thereof to form a conjugate between the probe and the reactive group and purifying the conjugate from excess reactive group. As discussed above, a probe may comprise a conventional (poly- or monoclonal) or a synthetic antibody or other binding molecule, a nucleic acid binding probe, a peptide nucleic acid probe capable of hybridizing to a specific nucleic acid sequence, a lipid binding molecule, a carbohydrate binding molecule. The present invention is advantageously carried out using probes with minimal negative steric effects on energy transfer efficiency between dyes attached to the probes. For example, an antibody probe smaller than a complete IgG, such as a Fab', Fab, a single chain Fv fragment or a diabody (scFv dimer) may advantageously be used. Furthermore, a low molecular weight fluorescent FRET pair can be used. Perhaps the most convenient and widely used functional group for the labeling of biological molecules is a primary amino group. This can be provided by the epsilon-amino group of a lysine residue, or the free N-terminus of a peptide/protein. Alternatively, it is possible to introduce primary amine containing modifier groups during automated synthesis of, for example, oligonucleotides. Stable active esters of fluor labeling species that may be stored as solid materials, in particular N-hydroxysuccinimide (NHS) esters have been extensively used over many years for the acylation of such amino groups. As an alternative to primary amino labeling, thiol containing groups such as those contained in cysteine residues or, as with primary amino groups, those introduced as modifiers during automated synthesis (of for example oligonucleotides) can be specifically targeted by maleimide labeling reagents (for example of Cy3 and Cy5). It is not always feasible to consider the use of either primary amino or thiol labeling on all biological molecules. A further common route for labeling of, for example, carbohydrate species is via an aldehyde group targeted by hydrazide labeling reagents.

A commercial kit may suitably be used for obtaining a probe set comprising at least two probes, each probe provided with a dye and additionally provided with a reactive group. Typically, labeling and purifying probe conjugates with such labeling kits can be readily accomplished in under three hours, with very little hands-on time. For example, there is a kit available for labeling a proteinaceous probe, e.g. an antibody or a peptide, with a fluorescent dye (www.probes.com/handbook/tables/157Q.html). The amount of dye necessary for the desired proteinaceous sample is calculated using the guidelines outlined in the kit's protocol. Generally, a reactive dye has a succinimidyl ester moiety that reacts efficiently with primary amines of a proteinaceous substance to form a stable dye—conjugate. Purification of a conjugate can be easily accomplished using a spin column or a size-exclusion spin column. The final coupling ratio can be determined according to standard procedures known to those skilled in the art. A dye to protein ration of approximately 2.5 to 1 often results in the retention of the ability of the probe to specifically recognize a molecule and in sufficient fluorescence for use of the FRET technique. Likewise, various commercial kits are available which can be used for labeling a probe with a reactive group, such as biotin. The biotin-XX sulfosuccinimidyl ester (SSE) is water soluble and reacts with a primary amine to form a stable biotin conjugate. The biotin-XX SSE has a 14-atom spacer that enhances the binding of biotin derivatives to avidin's relatively deep binding sites. A labeling kit typically contains a ready-to-use spin column for purification of a biotinylated probe from excess reagents.

The invention also provides a diagnostic test kit for the determination of interacting molecules in a biological sample comprising a set of probes according to the invention. In a preferred embodiment, the test kit provided comprising a probe set for FRET-mediated detection of interacting molecules is combined with one or more dye-conjugated antibodies that can be used for defining a target cell population within a mixture of cells. This is generally advantageous when the sample comprises a biological sample. For example, it permits identification and quantification of abnormal cells in a mixture of abnormal cells with normal cells, e.g. on the basis of defined abnormal signaling complexes. Many different types of abnormal signaling complexes can be detected in diagnostic applications using a method according to the invention. For example, the interaction of the RAG1 and RAG2 proteins in lymphoid leukemias that have ongoing rearrangements can be evaluated. Only in those cells where RAG1 and RAG2 dimers are tethered to the target DNA sequence, rearrangements are in progress. Another example involves the detection of an interaction of dephosphorylated beta-catenin with a member of the TCF family of transcription factors. Only in those cells where after cellular activation a signal is detected, the TCF factors are transcriptionally active. Thus, a method as provided herein provides means for monitoring, optionally at the single cell level, normal and pathological Wnt signaling, e.g. in colon carcinomas, melanomas, prostate cancer, breast cancer etc.

Furthermore, a method or a probe set of the invention is advantageously used in the area of drug discovery, for instance, to select a (candidate) drug compound from among a library of compounds. Following drug target identification, biopharmaceutical companies need a rapid system for screening the target against libraries of compounds to identify those compounds that will have an effect on the target and that demonstrate the potential to become effective drugs. In one embodiment, a FRET based method of the invention is used to screen for compounds which affect the interaction between two or more molecules in a cell, for instance, compounds that can stimulate or inhibit the formation of signaling complexes such as the signalosome. Hereto, a probe set is used comprising a first probe that is reactive with a first protein of the signaling complex and a second probe that is reactive with a second protein of the complex. When the complex is intact, the first and second protein interact such that the dye-conjugated probes are juxtaposed and a FRET signal can be detected. Upon addition of a compound (e.g., a drug candidate molecule) which binds to a component of the complex, the interaction between proteins within the complex is disrupted. As a result, the protein-bound probes are no longer juxtaposed and FRET no longer occurs. Of course, a similar approach can be undertaken to screen for compounds which stimulate or enhance an interaction between molecules. In that case, no FRET signal is detected in the absence of the compound but addition of the compound brings two or more molecules in close proximity of each other such that FRET occurs. In another embodiment, a method as provided herein is used to detect the interaction between a compound (drug) and its target, i.e. the interacting molecules are the compound and the target. This requires a set of probes wherein one probe is reactive with the compound and another probe that is reactive with the target (protein), for instance a compound-specific antibody probe and a target-specific antibody probe may be used. It can be imagined that the development of specific antibodies for hundreds of different compounds to be screened is not very attractive in e.g. a high throughput screening setting. However, one may provide different compounds with an identical (epitope) tag such that only one (antibody) probe directed against the tag can be used together with a target-specific probe for detecting the interaction between the compound and its target.

The invention provides a method for the detection of interacting proteins and other molecules using a set of at least a first and a second probe each probe provided with a dye wherein the dyes together allow energy transfer; at least one probe provided with a reactive group wherein the reactive group allows to modulate juxtaposing of the probes such that there is an increased likelihood of energy transfer between them. Preferably, yet not exclusively, a probe set according to the invention comprises a set of two dye-conjugated antibodies, each antibody additionally provided with a reactive group.

To exemplify the invention, we will describe the preparation of such a set of probes.

EXAMPLES

Probe Set Preparation.

Methods of producing an antibody are known to those skilled in the art, e.g. using hybridoma technology or phage display. To obtain a polyclonal antibody, a laboratory animal is immunized with an immunogen such as a recombinant protein or a synthetic peptide. The animal's immune response is monitored by taking test bleeds and determining the titer of the reactivity. When appropriately high titers are obtained, blood is collected from the animal and antisera are prepared. Further fractionation of the antisera to enrich for antibodies reactive to the protein can be done if desired. See e.g. Harlow et al. *Antibodies. A Laboratory Manual*, Cold Spring Harbor Publications, New York (1988). Monoclonal antibodies can be obtained by various techniques familiar to those skilled in the art. Antibodies obtained can be characterized conventional immunodiagnostic techniques e.g. by Western blotting using lysates of cells expressing a recombinant fusion protein or by ELISA.

Biotin Labeling of Antibodies

Biotin is typically conjugated to proteins via primary amines (i.e., lysines). Usually, between 3 and 6 biotin molecules are conjugated to each antibody. Dialyze or exchange over a column the antibody in 100 mM carbonate, pH 8.4. Measure the antibody concentration after buffer equilibration (For IgG, 1 mg/ml has an A(280) of 1.4). If the antibody concentration is less than 1 mg/ml, the conjugation will probably be sub-optimal. If necessary, dilute the antibody to a concentration of 4 mg/ml. Dissolve 10 mgs of Biotin (N-hydroxysuccinimidobiotin, Pierce) in 1 ml anhydrous DMSO (anhydrous dimethyl sulfoxide, Aldrich) immediately before use. The reactive biotin molecule is unstable. Once the biotin is solubilized, it should be used immediately. Add Biotin to give a ratio of 80 μg per mg of antibody; mix immediately. Wrap the tube in foil; incubate and rotate at room temperature for 2 hours. Remove the unreacted Biotin and exchange the antibody into 10 mM Tris pH 8.2, 150 mM NaCl, pHix (5 mg/ml pentachlorophenol in 95% ethanol (use as 10,000×, or 3-4 drops per liter) Sigma).

Fluorochrome Conjugation of a Probe

As discussed before, a large variety of dyes or fluorochromes can be used to label a probe according to the present invention. As an example, Cy5 conjugation of an antibody probe is given but of course many other fluorochromes can be chosen. The entire conjugation can typically be performed in about a half-day. The reactive Cy5 molecule is unstable. Open a vial, and weigh out the amount you need (typically, 1 or 2 mg is more than enough). Reseal the vial and store under desiccant at 4 degrees Celsius. Immediately dissolve the Cy5 in DMSO at a concentration of 10 mg/ml.

I. Preparation of Antibody.

Dialyze or exchange over a column the antibody in 500 mM carbonate, pH 9.5. Measure the antibody concentration after buffer equilibration. (For IgG, 1 mg/ml has an A(280) of 1.4). If the antibody concentration is less than 1 mg/ml, the conjugation will probably be sub-optimal. If necessary, dilute the antibody to a concentration of 4 mg/ml.

II. Covalent Conjugation

Cy5 is Covalently Coupled to Primary Amines (Lysines) of the Immunoglobulin.

Dissolve the Cy5 (Cy5-bis-OSU, N,N'-biscarboxypentyl-5,5'-disulfonatoindodicarbocyanine, Amersham Life Science) in anhydrous DMSO (dimethyl sulfoxide, Aldrich) immediately before use, at a concentration of 10 mg/ml. Do not delay between weighing out the Cy5 and dissolving it in DMSO; likewise, do not delay the addition of the solubilized material to the antibody. For the optimal ratio of 5:1, add 40 μg Cy5 per mg of antibody; mix immediately. Wrap the tube in foil; incubate and rotate at room temperature for 1 hour. Remove the unreacted Cy5 and exchange the antibody into 10 mM Tris pH 8.2, 150 mM NaCl, pHix (Sigma; 5 mg/ml pentachlorophenol in 95% ethanol (use as 10,000×, or 3-4 drops per liter), by gel filtration or dialysis.

REFERENCES

1. Mason D Y, Comans-Bitter W M, Cordell J L, et al, Antibody L26 recognizes an intracellular epitope on the B-cell-associated CD20 antigen. *Am J Pathol* 1990; 136: 1215-22.
2. Matyus L, Fluorescence resonance energy transfer measurements on cell surfaces. A spectroscopic tool for determining protein interactions. *J Photochem Photobiol B* 1992; 12: 323-37.
3. Chan F K, Siegel R M, Zacharias D, et al, Fluorescence resonance energy transfer analysis of cell surface receptor interactions and signaling using spectral variants of the green fluorescent protein. *Cytometry* 2001; 44: 361-8.
4. Siegel R M, Chan F K, Zacharias D A, et al, Measurement of molecular interactions in living cells by fluorescence resonance energy transfer between variants of the green fluorescent protein. *Sci STKE* 2000; 2000: L1.
5. Wouters F S, Bastiaens P I. Fluorescence lifetime imaging of receptor tyrosine kinase activity in cells. *Curr Biol* 1999; 9:1127
6. Guo C, Dower S K, Holowka D, Baird B. Fluorescence resonance energy transfer reveals interleukin (IL)-1-dependent aggregation of IL-1 type I receptors that correlates with receptor activation. *J Biol Chem* 1995; 270:27562
7. Broudy V C, Lin N L, Buhring H J, et al, Analysis of c-kit receptor dimerization by fluorescence resonance energy transfer. *Blood* 1998; 91:898-906.
8. Szollosi J, Damjanovich S, Matyus L, Application of fluorescence resonance energy transfer in the clinical laboratory: Routine and research. *Cytometry* 1998; 34:159
9. Tanke, H J. Fluorochromen voor twee- en drievoudige labelingen. *Immunofenotypering in de diagnostiek: indicatiestellingen, uitvoering en interpretatie.* Eds. Van Dongen, Groeneveld, Adriaansen., Hooijkaas (ISBN 90-73436-16-8). 1994; pages 55-61.
10. Chen R, Kang V H, Chen J, et al. A monoclonal antibody to visualize PtdIns(3,4,5)P(3) in cells. *J Histochem Cytochem.* 2002; 50(5):697

What is claimed is:

1. A set of probes comprising at least first and second molecular probes, each said molecular probe provided with a dye, wherein said dyes together allow energy transfer, each molecular probe comprising a binding domain able to specifically bind a molecule of interest, and wherein said first molecular probe is provided with at least one reactive group allowing a juxtaposition of said at least first and second molecular probes and wherein said at least one reactive group is not involved in binding to the molecule of interest, and wherein said at least one reactive group of said first molecular probe is not directly reactive with said second molecular probe.

2. The set of probes of claim 1 wherein said reactive group allows the juxtaposition of said dyes at a distance selected from the group consisting of within a distance of 100 Ångstrom of each other, within a distance of 50 Ångstrom of each other, and within a distance of 20 Ångstrom of each other.

3. The set of probes of claim 1, wherein at least one molecular probe is provided with a multiplicity of said reactive groups.

4. The set of probes of claim 1, wherein said molecular probe is an antibody or otherwise comprises an antibody binding fragment.

5. The set of probes of claim 1, wherein at least one molecular probe is a nucleic acid.

6. The set of probes of claim 1, wherein at least one of said dyes is a fluorochrome.

7. The set of probes of claim 6 wherein said fluorochrome is selected from the group consisting of fluorescein isothiocyanate (FITC), tetramethylrhodamine isothiocyanate (TRITC), Texas Red (TR), R-phycoerythrin (R-PE), allophycocyanin (APC), members of the phycobiliproteins, Cy3, Cy5, Cy5.5, Cy7, cyanine dyes, Alexa Fluor dyes, tandem conjugates thereof, and quantum dot dyes.

8. The set of claim 1 wherein said reactive group is biotin.

9. A method for detecting at least two interacting molecules in a cell using a set comprising at least a first and a second molecular probe, each molecular probe provided with a dye wherein said dyes together allow energy transfer and each molecular probe comprising a binding domain able to specifically bind a different molecule of interest, wherein at least one molecular probe is provided with a reactive group that is not involved in binding to a molecule of interest but allows for juxtaposing said at least first and second molecular probes such that there is an increased likelihood of energy transfer between said dyes, said method comprising:
providing a set of molecular probes,
providing a sample comprising a cell,
contacting said sample with said set of molecular probes under conditions that allow juxtaposing said molecular probes on said interacting molecules, and
detecting juxtaposition of said molecular probes via FRET to detect said interacting molecules.

10. A method for detecting at least two interacting molecules in a cell using a set of at least a first and a second molecular probe, each molecular probe provided with a dye wherein said dyes together allow energy transfer and each probe comprising a binding domain able to specifically bind to a different molecule of interest, wherein at least one molecular probe is provided with a reactive group that is not involved in binding to a molecule of interest but allows for juxtaposing said at least first and second molecular probes such that an increased likelihood of energy transfer between said dyes exists, wherein a reactive group of said first molecular probe is not directly reactive with said second molecular probe, said method comprising:
providing a set of at least the first and the second molecular probes,
providing a sample comprising a cell,
contacting said sample with said set of molecular probes under conditions that allow juxtaposing said molecular probes on said interacting molecules,
contacting said molecular probes with a substance able to link at least a reactive group of said first molecular probe to said second molecular probe, and
detecting juxtaposition of said molecular probes via FRET to detect said interacting molecules.

11. The method according to claim 10 wherein said substance allows juxtaposing said dyes within a distance of from about 2 to about 100 Angstroms of each other.

12. The method according to claim 10 wherein said reactive group comprises biotin and wherein said substance comprises avidin or streptavidin.

13. The method according to claim 9, including staining said sample for at least one cellular marker to define a target cell population comprising:
contacting said sample with a compound able to selectively bind to said cellular marker.

14. The method according to claim 9, wherein at least one of said molecules is selected from the group consisting of a proteinaceous substance, a nucleic acid, a lipid molecule, and a carbohydrate.

15. The method according to claim 9, further comprising detecting at the single cell level.

16. A method for providing at least a first and a second molecular probe, each molecular probe provided with a dye, wherein said dyes together allow energy transfer, each molecular probe comprising a binding domain able to specifically bind to a molecule of interest, wherein at least one molecular probe is provided with a reactive group allowing juxtaposing said at least first and second molecular probes and wherein said reactive group is not involved in binding to the molecule of interest, said method comprising:
providing molecular probes able to specifically bind to a molecule of interest,
contacting each molecular probe with a suitable dye to form a conjugate between said molecular probe and said dye, and
contacting at least one molecular probe with a reactive group or a derivative thereof to form a conjugate between said molecular probe and said reactive group.

17. The method according to claim 16 wherein said reactive group comprises biotin.

18. A diagnostic kit comprising the set of probes of claim 1.

19. A method of diagnosing and/or classifying a disease state in a subject before, during, or after treatment to evaluate the effectiveness of said treatment or to diagnose and/or classify the disease state, comprising:
analyzing a sample obtained from the subject with a set of probes before, during or after treatment of a disease to evaluate the effectiveness of said treatment or to diagnose and/or classify a disease;
wherein the set of probes comprise at least first and second molecular probes, each said molecular probe provided with a dye, wherein said dyes together allow energy transfer, each molecular probe comprising a binding domain able to specifically bind a molecule of interest, and wherein at least one molecular probe is provided with at least one reactive group, said at least one reactive group allowing a juxtaposition of said at least first and second molecular probes and wherein said reactive group is not involved in binding to the molecule of interest.

20. An improvement in a method of selecting a drug compound from among a library of compounds, the improvement comprising:
using a probe set to select the drug compound from among the library of compounds;
wherein the probe set comprises at least first and second molecular probes, each said molecular probe provided with a dye, wherein said dyes together allow energy transfer, each molecular probe comprising a binding domain able to specifically bind a molecule of interest, and wherein at least one molecular probe is provided with at least one reactive group, said at least one reactive group allowing a juxtaposition of said at least first and second molecular probes and wherein said reactive group is not involved in binding to the molecule of interest.

21. The method according to claim 13, wherein said cellular marker is a cluster of differentiation (CD) antigen.

22. The method according to claim 15, wherein detecting at the single cell level utilizes flow cytometry.

23. A set of probes comprising at least first and second molecular probes, each said molecular probe provided with a dye, wherein said dyes together allow energy transfer, each molecular probe comprising a binding domain able to specifically bind a molecule of interest, and wherein at least one molecular probe is provided with at least one reactive group comprising biotin, said at least one reactive group allowing a juxtaposition of said at least first and second molecular probes and wherein said reactive group is not involved in binding to the molecule of interest.

* * * * *